(12) United States Patent
Brittain et al.

(10) Patent No.: US 7,934,070 B2
(45) Date of Patent: *Apr. 26, 2011

(54) STREAMING READS FOR EARLY PROCESSING IN A CASCADED MEMORY SUBSYSTEM WITH BUFFERED MEMORY DEVICES

(75) Inventors: Mark Andrew Brittain, Pflugerville, TX (US); Edgar Rolando Cordero, Round Rock, TX (US); Sanjeev Ghai, Round Rock, TX (US); Warren Edward Maule, Cedar Park, TX (US)

(73) Assignee: International Business Machines Corporation, Armonk, NY (US)

( * ) Notice: Subject to any disclaimer, the term of this patent is extended or adjusted under 35 U.S.C. 154(b) by 9 days.

This patent is subject to a terminal disclaimer.

(21) Appl. No.: 11/951,752

(22) Filed: Dec. 6, 2007

(65) Prior Publication Data

US 2008/0091906 A1 Apr. 17, 2008

Related U.S. Application Data

(63) Continuation of application No. 11/054,466, filed on Feb. 9, 2005, now abandoned.

(51) Int. Cl.
*G06F 12/00* (2006.01)

(52) U.S. Cl. ....................................................... 711/167

(58) Field of Classification Search ........................ None
See application file for complete search history.

(56) References Cited

U.S. PATENT DOCUMENTS

| | | | | |
|---|---|---|---|---|
| 7,277,988 B2 * | 10/2007 | Gower et al. | ................... | 711/118 |
| 7,337,293 B2 * | 2/2008 | Brittain et al. | ................ | 711/167 |
| 7,389,387 B2 * | 6/2008 | David | .......................... | 711/143 |
| 2002/0129215 A1 * | 9/2002 | Yoo et al. | ...................... | 711/167 |

* cited by examiner

*Primary Examiner* — Hiep T Nguyen
(74) *Attorney, Agent, or Firm* — Dillon & Yudell LLP (57) ABSTRACT

A memory subsystem completes multiple read operations in parallel, utilizing the functionality of buffered memory modules in a daisy chain topology. A variable read latency is provided with each read command to enable memory modules to run independently in the memory subsystem. Busy periods of the memory device architecture are hidden by allowing data buses on multiple memory modules attached to the same data channel to run in parallel rather than in series and by issuing reads earlier than required to enable the memory devices to return from a busy state earlier. During scheduling of reads, the earliest received read whose target memory module is not busy is immediately issued at a next command cycle. The memory controller provides a delay parameter with each issued read. The number of cycles of delay is calculated to allow maximum utilization of the memory modules' data bus bandwidth without causing collisions on the memory channel.

17 Claims, 8 Drawing Sheets

STREAMING READS FOR EARLY PROCESSING IN A CASCADED MEMORY SUBSYSTEM WITH BUFFERED MEMORY DEVICES

PRIORITY CLAIM

The present application is a continuation of U.S. patent application Ser. No. 11/054,446, entitled, "Streaming Reads For Early Processing In A Cascaded Memory Subsystem With Buffered Memory Devices, filed Feb. 9, 2005 now abandoned.

CROSS REFERENCE TO RELATED APPLICATION(S)

The present invention is related to the following commonly assigned, co-pending applications: "Write Command Execution in Buffered DIMM Configuration," Ser. No. 11/054,447; "Execution of Background Writes to Idle DIMMS," Ser. No. 11/054,372; "Power Management Via DIMM Read Operation Limiter," Ser. No. 11/054,066; and "Dynamic Power Management With DIMM Read Operation Limiter," Ser. No. 11/054,392; all filed concurrently herewith. The contents of the above applications are incorporated herein by reference.

BACKGROUND OF THE INVENTION

1. Technical Field

The present invention relates generally to computer devices and in particular to memory subsystems. Still more particularly, the present invention relates to a method and system for efficiently completing read operations within memory subsystems.

2. Description of Related Art

Improvements in computer memory subsystems continue to be one of the major developments that enable more efficient and faster computer systems. A historical perspective of the evolution of computer memory subsystems is provided in commonly assigned and co-pending patent application Ser. No. 10/903,178, and its related applications, relevant content of which is incorporated herein by reference.

Figure 2A:
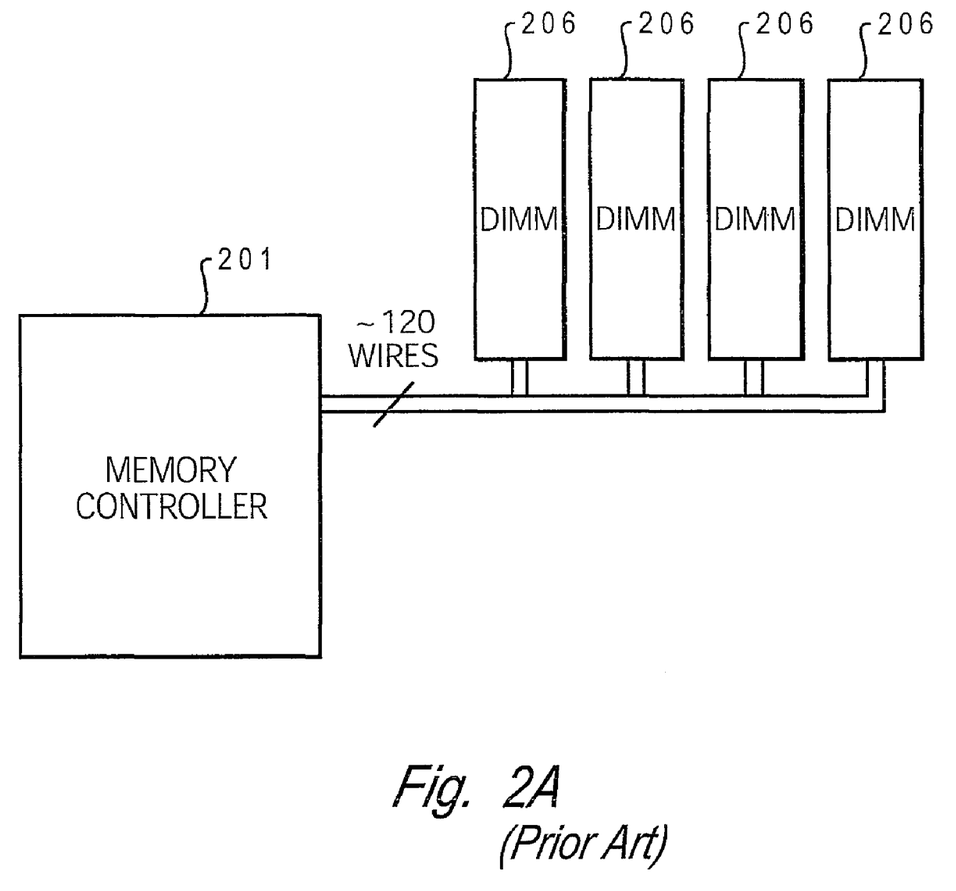
FIGS. 2A and 2B depict two illustrations of a memory subsystem with DIMMS dotted to the same address and data buses according to the prior art.
Figure 2B:
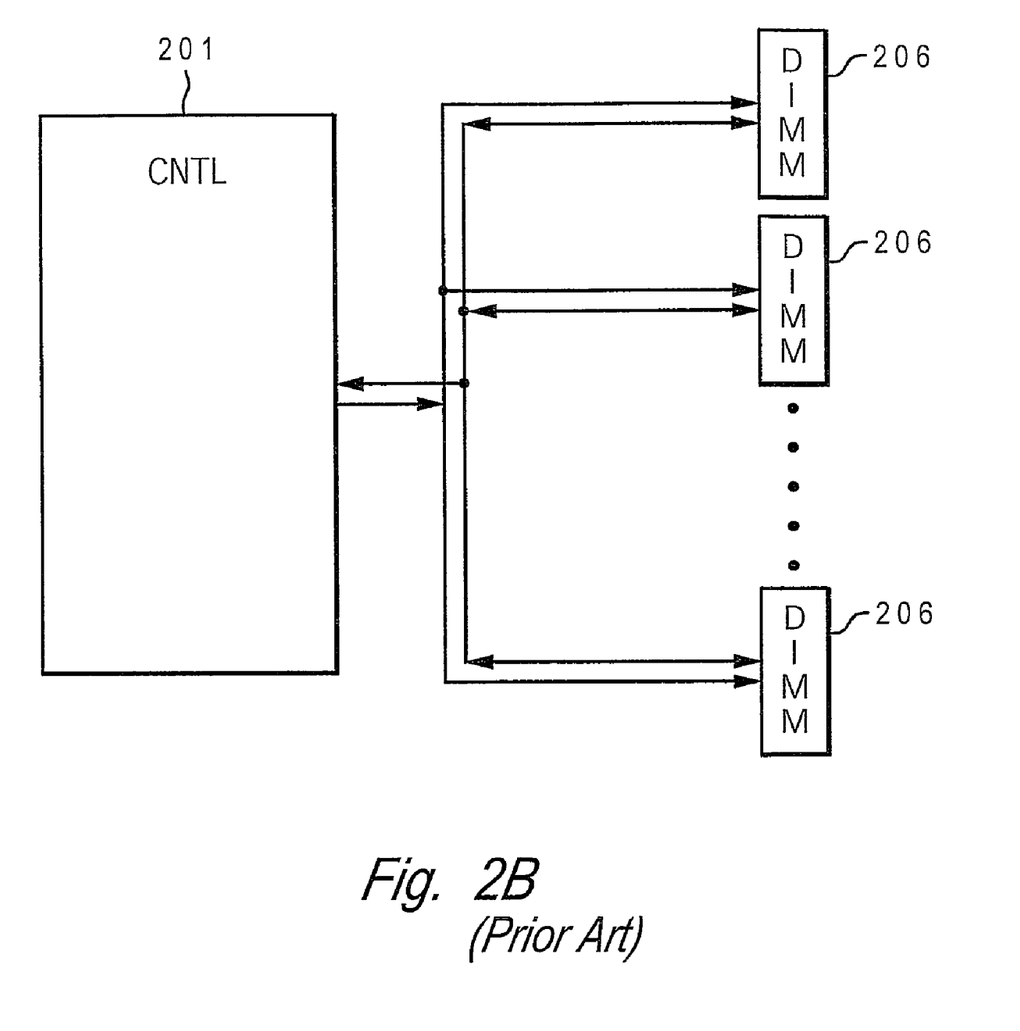

As recited in that application, computer memory subsystems have evolved from point-to-point bus topology of the early 1980's (e.g., U.S. Pat. No. 4,475,194) to more recent computer memory subsystems, which includes up to four registered dual inline memory modules (DIMMs) on a traditional multi-drop stub bus channel (e.g., U.S. Pat. No. 6,510,100). This latter structure has inherent limits on the number of modules that may be attached to the stub bus due to the increasing data rate of the information transferred over the bus. FIGS. 2A and 2B illustrate prior art memory subsystems configured with multiple DIMMs 206 connected to a memory controller 201 via a stub bus topology. As shown, all memory modules (DIMMs) 206 connect directly to a single system address/command bus and a single system bi-directional data bus.

Figure 1:
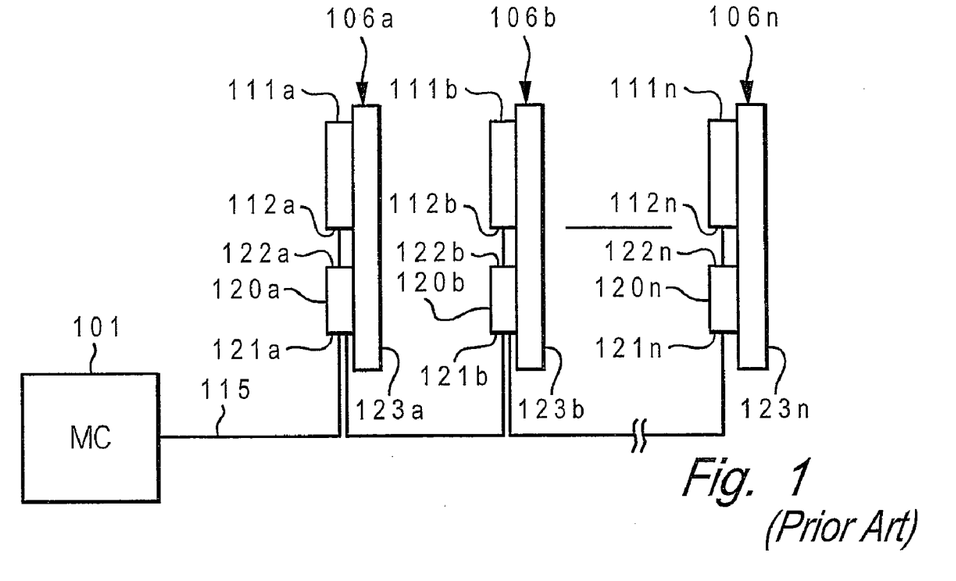
FIG. 1 depicts a prior art daisy chain connection between a memory controller and memory modules.

Further development led to the introduction of the daisy chain topology (U.S. Pat. No. 4,723,120), which provides point-to-point interfaces to separate devices. FIG. 1 illustrates a prior art daisy-chained memory channel, implemented consistent with the teachings in U.S. Pat. No. 4,723,120. According to the configuration, memory controller 110 is connected to a memory channel 115, which further connects to a series of memory modules 106a-n. Each module 106a-n includes a DRAM 111a-n and a buffer 120a-n. The information on memory channel 115 is re-driven by the buffer 120a on module 106a to the next module 106b, which further re-drives the channel 115 to module positions denoted as 106n. Within conventional systems, each memory module is a dynamic inline memory module (DIMM).

One drawback to the use of a daisy chain bus topology is increased latency associated with the return of read data via the series of daisy chained memory modules. Because each module in the channel has a different number of intervening stages to return data to the memory controller, each module has different latency for returning data to the memory controller. The variations in latencies among memory modules present a management problem for the memory controller, particularly since collisions on the memory channel have to be avoided.

One solution presented for handling these varying latencies associated with the memory modules involves leveling the read data latency of all the modules by setting the latency of modules closer to the memory controller (i.e., those with shorter latencies) equal to the latency of the module that is furthest away from the memory controller in the chain. Leveling the data return latency in this manner can be achieved by adding a fixed amount of delay to the return of read data based on the data's location in the channel. In this way, the memory controller will receive all read data with the same latency following the issuance of the read request/command, regardless of the location of the target memory module within the chain.

Additional cycles of delay were thus added to each of the closer memory modules and these delays were coded into the buffer logic of the memory module. The buffer logic is then used to delay the placement of the requested data on the memory channel for the preset number of cycles to allow for equal return data latencies.

Forcing all read operations to complete at the worst-case latency severely limits the efficiency of the memory subsystem and adds unnecessary delays in the data retrieval process. Further, with the prior art implementation, read requests must be issued at fixed times to line up with openings in the returning data stream. This requirement can result is unused data cycles on the read data channel when there is a conflict between two commands that need to be issued on the address bus. The combination of these two requirements limits the efficiency of the memory channel by adding unnecessary latency and idle cycles on the memory data channel.

One advantage of the daisy chained implementation is that each memory module installed on the data channel has an independent data bus to its DRAMs. Although all the memory modules share the same data channel back to the memory controller, they individually have a separate data bus that is isolated from the memory channel by the buffer chip. Data bandwidth in a DRAM memory system is affected by a number of DRAM architecture requirements, and the data bus bandwidth generally falls well short of the maximum available bandwidth of the common data bus, in this case the daisy chained memory channel. Therefore having multiple independent data buses driving a single memory channel may significantly increase the data bandwidth available in the system.

In the prior art implementations of the daisy channel memory system the requirement that all memory modules return data with the latency of the last memory module in the chain effectively results in a configuration where all the memory module data buses run as if they were one bus. This reduces the available bandwidth in the system back to that provided by the traditional multi-drop stub bus configurations and results in inefficient usage of the data bandwidth on the daisy chained memory channel.

The present invention thus recognizes that it would be desirable to allow each memory module data bus to run independently thus increasing overall data bus bandwidth. The invention further recognizes that it would be desirable to hide the inefficiencies of the DRAM architecture due to the busy time incurred after each operation.

SUMMARY OF THE INVENTION

Disclosed is a method and system for efficiently completing multiple read operations within a memory subsystem having a memory controller coupled to buffered memory modules in a daisy chain topology. A variable read latency is provided with each read command issued to allow the data bus on each memory module that is installed on the memory channel to run independently of all other memory modules on the channel. The inefficiency of the DRAM architecture are hidden by allowing data buses on multiple memory modules attached to the same memory channel to run in parallel rather than in series and by issuing reads earlier than required to enable the DRAMs to return from a busy state earlier. Data from the early read requests will be buffered on the individual memory modules and streamed out to the memory channel at a later time to fill up the available data slots on the memory channel.

The memory controller maintains a history of the issued reads and the time data is scheduled to be returned and issues a delay parameter with each issued read to line up the data with the next available data opening on the memory channel. Each memory module has one or more read data buffers utilized for holding data returned by a read operation at the memory module for a pre-calculated number of cycles. The delay parameter alerts the buffer logic of the memory module how long the data in the particular buffer is to be delayed within the buffer before being placed on the memory channel. The number of cycles of delay is calculated to allow maximum utilization of the system's memory channel. The issuance of multiple reads is thus able to be completed over sequential command cycles so that reads occur in parallel across the different memory modules, and the memory modules are returned from a busy state earlier than with conventional issuance of reads.

This disclosed method improves the efficiency of the memory channel by executing read commands on the memory modules at the earliest time that the DRAM architecture will allow versus delaying the read until there is a window for the data on the memory channel. This will allow future reads operations to the same memory module to execute earlier, therefore reducing latency of these read operations. In addition, by reading data from multiple memory modules at the same time the memory subsystem will buffer read data internal to the memory modules that can be used to fill open slots on the memory channel that result from DRAM architecture restrictions on the memory modules.

In one embodiment, the memory controller will issue read operations to the memory modules at a rate to maximize the data bus internal to the memory module. The combined data rate from all the memory modules on the channel may be higher than the available bandwidth on the channel. The excesses data is stored in buffers on the memory modules and streamed to the channel as bandwidth is available. In effect this method allows memory operations to be retired early from the memory controller and allows the memory module to return to an idle state at an earlier time. This allows subsequent reads to the same memory module to execute earlier in time and therefore improves the overall latency and bandwidth of the memory subsystem.

The above as well as additional objectives, features, and advantages of the present invention will become apparent in the following detailed written description.

BRIEF DESCRIPTION OF THE DRAWINGS

The invention itself, as well as a preferred mode of use, further objects, and advantages thereof, will best be understood by reference to the following detailed description of an illustrative embodiment when read in conjunction with the accompanying drawings, wherein.

DETAILED DESCRIPTION OF ILLUSTRATIVE EMBODIMENTS

The present invention provides a method and system for efficiently completing multiple read operations within a memory subsystem having a memory controller coupled to buffered memory modules in a daisy chain topology. A variable read latency is provided with each read command issued to allow the data bus on each memory module that is installed in the memory subsystem to run independently in the memory subsystem. Additionally, inefficiencies of the memory device architecture are hidden by allowing data buses on multiple memory modules attached to the same data channel to run in parallel rather than in series and by issuing reads earlier than required to enable the memory devices to return from a busy state earlier.

For simplicity in describing the invention, the memory modules are assumed to be dual inline memory modules (DIMMs) and the memory devices are assumed to be Dynamic Random Access Memory (DRAMs). These modules contain multiple DRAMs arranged in groups to form one or more ranks of memory with each rank of memory containing one or more banks of memory. Those skilled in the art appreciate that specific references to these components, namely DIMMs and DRAMs, are not meant to be limiting on the invention, which finds applicability in any memory module having one or more memory devices thereon. These terms are utilized interchangeably throughout the description.

As described herein, issuing each read operation from the memory controller to a bank of memory on a memory module takes a known number of cycles (N), and a next read cannot be issued to that individual memory bank until N cycles following the previous read. This is referred to as the busy time of the memory bank. A second factor in issuing read operations is the busy time of the data bus. When a read is issued to a memory bank on a memory module, the result is a data packet that is generally 4 or 8 data cycles in length. Since all data uses a common data bus within the memory module another read cannot be issued within a 4 or 8 cycle window (depending on the data length of the previous read operation) of the first read operation. The two of these busy times are referred to within this invention as the memory module busy time. References to sequential issuing of reads to the system's address/command/control bus refer to issuing a next read at the next available command cycle at which a read may be issued.

A read-reorder queue is provided within the memory controller to schedule continuous issuance of reads according to which of the target memory modules is not currently busy. Idle bandwidth within the memory modules (DIMMs) is identified for utilization, and the earliest received read whose target memory module is not busy is immediately issued as a next read on the memory channel. Each memory module has one or more read data buffers utilized for holding data returned by a read operation at the memory module for a pre-calculated number of cycles.

The memory controller maintains a history of the issued reads and the time data is scheduled to be returned and issues a delay parameter with each issued read to line up the data with the next available data opening on the memory channel. Each memory module has one or more read data buffers utilized for holding data returned by a read operation at the memory module for a pre-calculated number of cycles. The delay parameter alerts the buffer logic of the memory module how long the data in the particular buffer is to be delayed within the buffer before being placed on the memory channel. The number of cycles of delay is calculated to allow maximum utilization of the system's memory channel. The issuance of multiple reads is thus able to be completed over sequential command cycles so that reads occur in parallel across the different memory modules, and the memory modules are returned from a busy state earlier than with conventional issuance of reads.

In the prior art, reads are issued based on the return cycle of data. Thus, if a read takes 4 cycles to issue and the data return takes 16 cycles, for example, the next read is not issued until 16 cycles following the first read in order to avoid data collisions on the memory channel. Reads thus are completed in a sequential manner, one at a time within the memory modules, with dead cycles between each issued read command.

The invention removes this built-in delay of cycles for issuing subsequent reads by buffering the data returned by the read operation for a number of cycles calculated to maximize use of the available bandwidth on the memory channel and prevent data collisions on the memory channel. Thus, according to the invention, the issuance of multiple reads is completed over sequential read cycles so that reads occur in parallel across the different memory modules, and the memory modules are returned from a busy state earlier than with conventional issuance of reads.

In one embodiment, the memory controller will issue read operations to the memory modules at a rate to maximize the data bus internal to the memory module. The combined data rate from all the memory modules on the channel may be higher than the available bandwidth on the channel. The excesses data is stored in buffers on the memory modules and streamed to the channel as bandwidth is available. In effect this method allows memory operations to be retired early from the memory controller and allows the memory module to return to an idle state at an earlier time. This allows subsequent reads to the same memory module to execute earlier in time and therefore improves the overall latency and bandwidth of the memory subsystem.

In one embodiment, rather than provide buffers on the memory modules, the buffers associated with each memory module is built on the backplane of the memory subsystem. The memory modules (DIMMs) are plugged into slots connected to the respective set of buffers and buffering of data retrieved from the DIMM occurs similarly to when the buffers are on the memory modules themselves. Larger numbers of buffers may then be provided for each memory module, which is able to accommodate more onboard memory devices.

In another embodiment, during an initial processing of the first reads of an application, data may be returned from the memory modules out of order relative to the order in which the read requests are issued, and the memory controller is able to correctly match each returned data with its read based on the pre-assigned return period (or delay cycles) associated with the read operation when issued. Reads issued to a last memory module with a return latency greater than a second read issued to a closer memory module are made to return data out of order and the memory module matches the first returned data to the second read and second returned data to the first read, etc.

Handling Reads in Cascade Memory Modules with Varying Latencies

Exemplary embodiments of the present invention provide circuits and methods that enable positional read data latency for a memory channel comprised of cascaded, buffered memory modules. The use of positional read data latency for a memory channel (also referred to herein as a memory subsystem) may lead to increased memory channel performance.

In an exemplary embodiment of the present invention, positional read data latency is provided by a high speed and high reliability memory subsystem architecture and interconnect structure that includes single-ended point-to-point interconnections between any two subsystem components. An alternate exemplary embodiment of the present invention utilizes differential interconnections between any two subsystem components. The memory subsystem further includes a memory controller function, one or more memory modules, one or more high speed busses operating at an integer (such as four to one) speed ratio relative to a DRAM data rate and a bus-to-bus converter chip on each of one or more cascaded modules to convert the high speed bus(ses) into the conventional double data rate (DDR) memory interface.

The memory modules operate as slave devices to the memory controller, responding to commands in a deterministic or non-deterministic manner. Memory modules can be added to the cascaded memory channel with each module assigned an address to permit unique selection of each module on the cascaded memory channel.

Exemplary embodiments of the present invention include a packetized multi-transfer interface which utilizes an innovative communication protocol to permit memory operation to occur on a reduced pin count, whereby address, command and data is transferred between the components on the cascaded bus over multiple cycles, and are reconstructed and errors corrected prior to being used by the intended recipient.

Figure 3A:
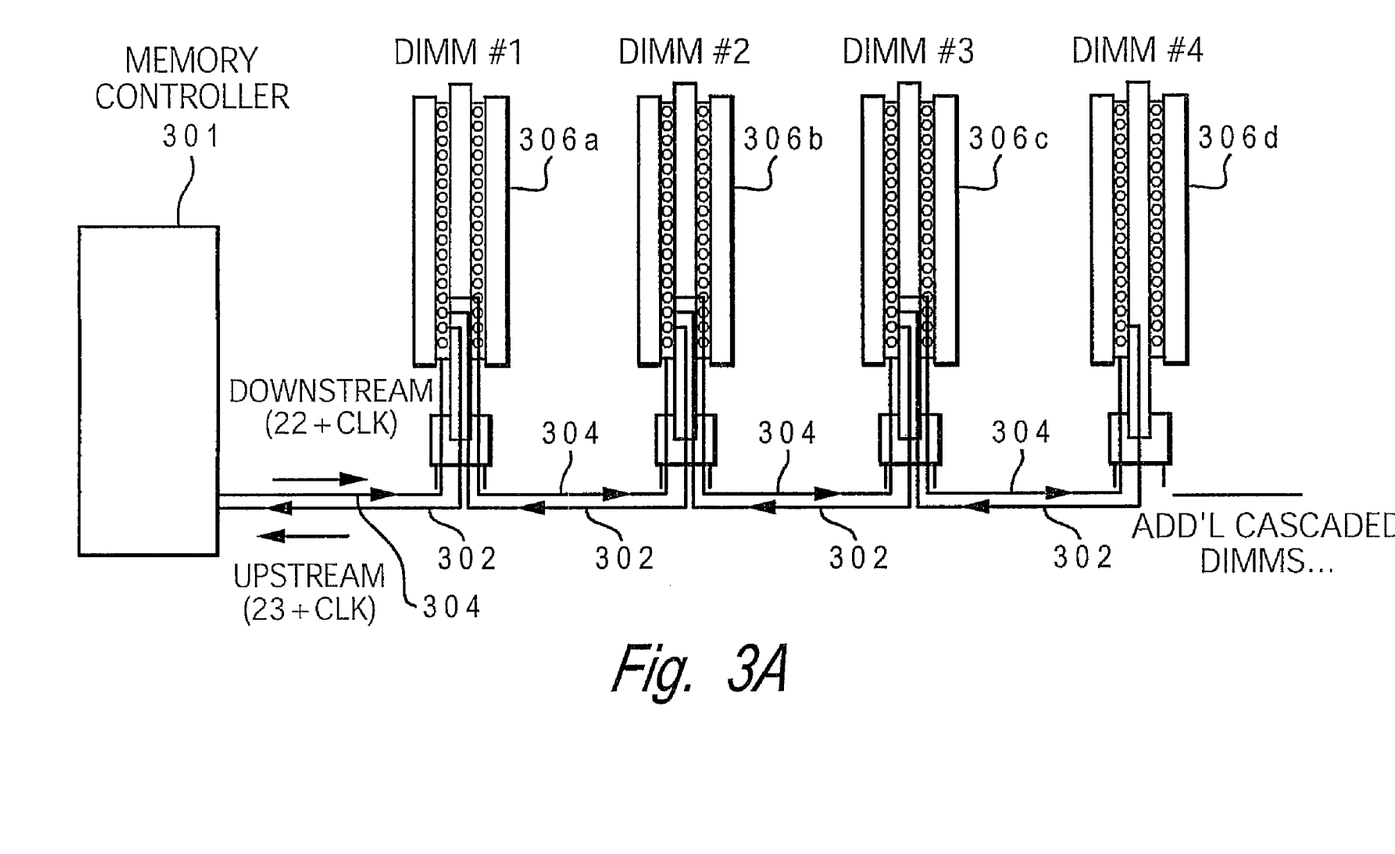
FIGS. 3A and 3B depict two illustrations of cascaded memory modules of a memory subsystem connected via unidirectional point-to-point busses according to two exemplary embodiments of the present invention.
Figure 3B:
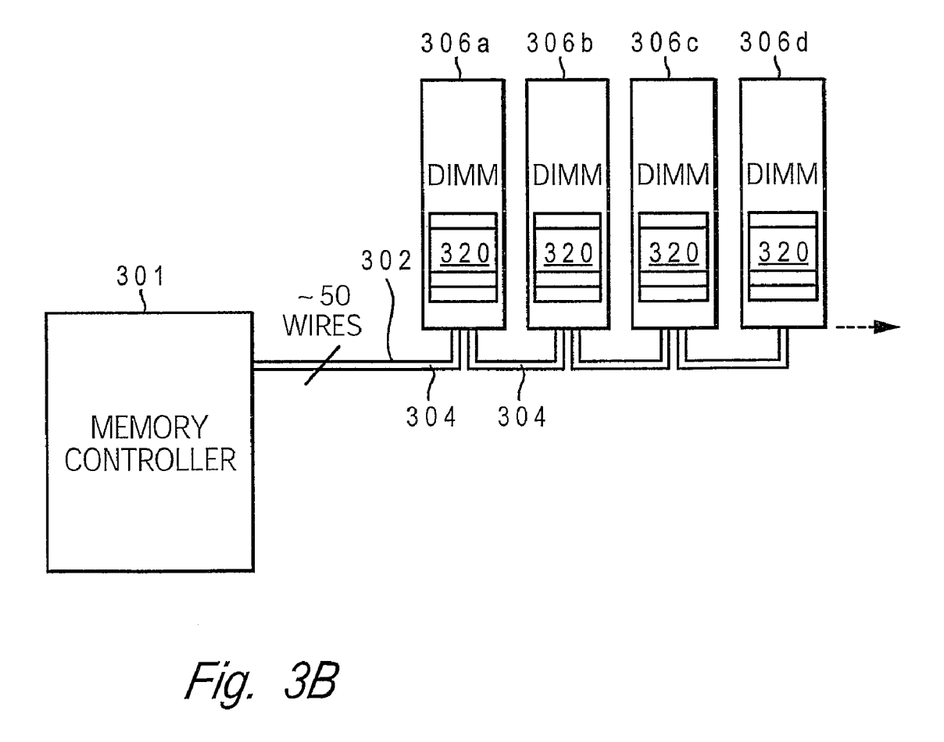

FIGS. 3A and 3B depict two configurations of a memory subsystem with cascaded, buffered memory modules and unidirectional busses that are utilized by exemplary embodiments of the present invention. This memory structure includes a memory controller 301 in communication with one or more memory modules 306a-d via a high speed point-to-point bus 304. One of the functions provided by the memory modules 306a-d in the cascade structure is a re-drive function to send signals on the memory bus to other memory modules 306a-d or to the memory controller 301. FIG. 3A-3B include the memory controller 301 and four memory modules 306a-306d, on each of two memory busses, a downstream memory bus (address/command/control bus) 304 and an upstream memory bus (or memory channel) 302, connected to the memory controller 302. Memory module 306a is connected to the memory controller 301 in a direct manner. Memory modules 306b, 306c and 306d are connected to the memory controller 301 in a cascaded manner.

The memory controller 301 interfaces to the memory modules 306 via a pair of high speed busses (or channels). An exemplary embodiment of the present invention includes two unidirectional busses between the memory controller 301 and memory module 306a ("DIMM #1"), as well as between each successive memory module 306b-d ("DIMM #2", "DIMM #3" and "DIMM #4") in the cascaded memory structure. The downstream memory bus 304 (outbound from the memory controller 301) interface has twenty-four pins and the upstream memory bus 302 (inbound to the memory controller 301) interface has twenty-five pins.

The downstream memory bus 304 is used to transfer address, control, write data and bus-level error code correction (ECC) bits downstream from the memory controller 302, over several clock cycles, to one or more of the memory modules 306 installed on the cascaded memory channel. The upstream memory bus 302 is used to transfer read data and bus-level ECC bits upstream from the sourcing memory module 306 to the memory controller 301. Using this memory structure, and a four to one data rate multiplier between the DRAM data rate (e.g., 400 to 200 Mb/s per pin) and the unidirectional memory bus data rate (e.g., 1.6 to 2.2 Gb/s per pin), the memory controller 301 signal pin count, per memory channel, is reduced from approximately one hundred and twenty pins to about fifty pins.

Due to the cascaded memory structure, all nets are point-to-point, allowing reliable high-speed communication that is independent of the number of memory modules 306 installed. Whenever a memory module 306 receives a packet on either bus, it re-synchronizes the command to the internal clock and re-drives the command to the next memory module 306 in the chain (if one exists).

Each bus 304 in the exemplary embodiment depicted in FIG. 3A-3B includes approximately fifty high speed wires for the transfer of address, command, data and clocks. By using point-to-point busses as described in the aforementioned prior art, it is possible to optimize the bus design to permit significantly increased data rates, as well as to reduce the bus pincount by transferring data over multiple cycles. An exemplary embodiment of the present invention, as depicted in FIG. 3A-3B, provides a four to one bus speed ratio to maximize bus efficiency and to minimize pincount.

Although point-to-point interconnects permit higher data rates, overall memory subsystem efficiency must be achieved by maintaining a reasonable number of memory modules 306 and memory devices per channel (historically four memory modules with four to thirty-six chips per memory module, but as high as eight memory modules per channel and as few as one memory module per channel). Using a point-to-point bus necessitates a bus re-drive function on each memory module. The re-drive function permits memory modules to be cascaded such that each memory module is interconnected to other memory modules, as well as to the memory controller 301.

Figure 4:
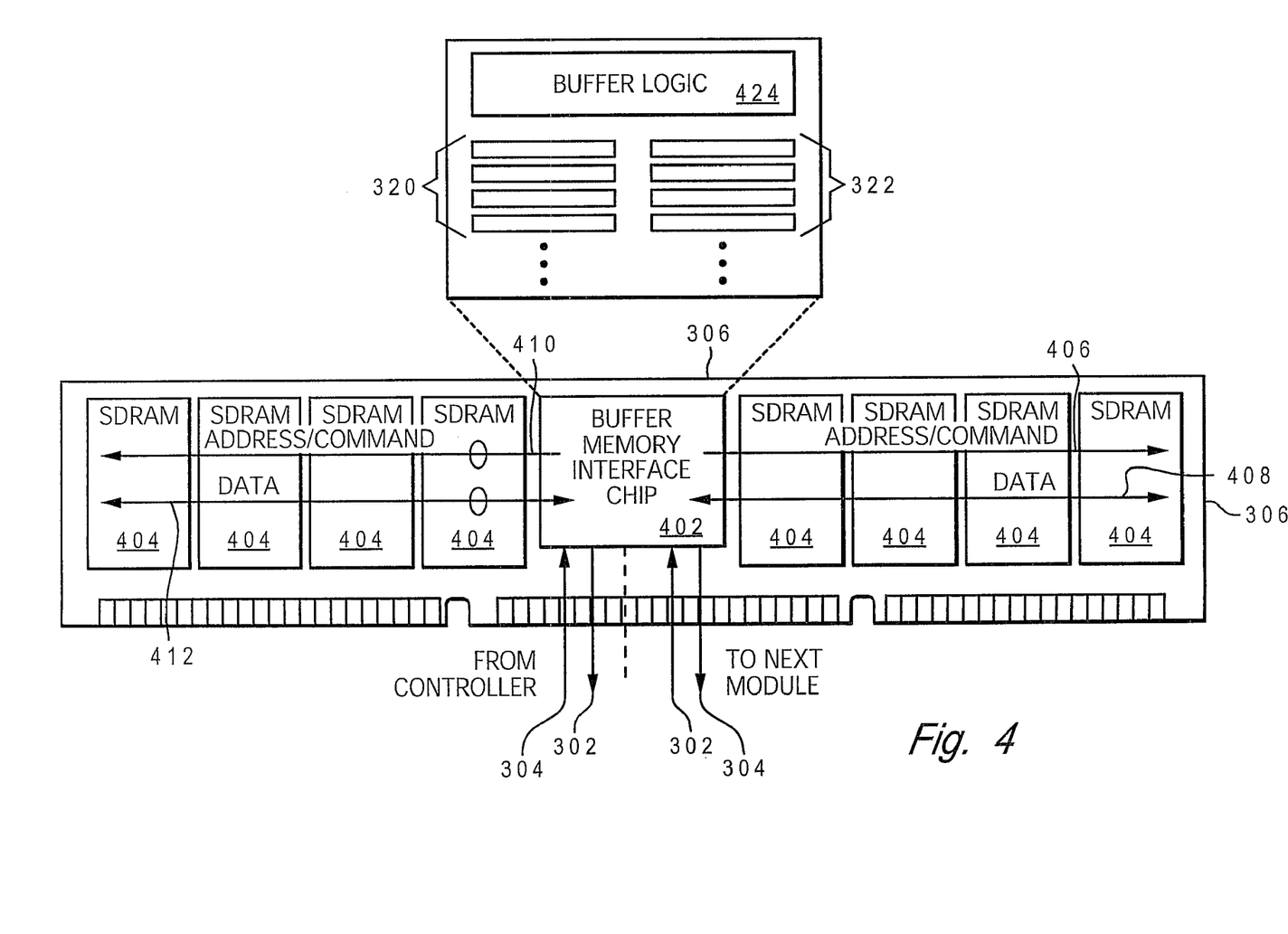
FIG. 4 depicts a buffered memory module with internal read buffers and on-module buses utilized to access the memory devices within one exemplary embodiment of the present invention.

FIG. 4 is a pictorial representation of a bus wiring scheme for a memory module within on-module buffers and control logic according to one embodiment of the invention. The primary signal flows are represented by shaded arrows and include the upstream memory bus (memory channel) 302, the downstream memory bus 304, memory device address and command busses 410 and 406, and memory device data busses 412 and 408.

In an exemplary embodiment of the present invention, illustrated by the insert above memory module 306, the buffer device 402, also referred to as a memory interface chip, includes multiple buffers and buffer logic. According to the invention, the buffers are designed with a delay logic/mechanism that enables the commands to be sent to the DRAMs ahead of time because the returning data is placed in the buffer and held until the pre-set number of cycles passes. Unlike a staging latch provided by some convention designs, the invention provides a complete/full holding buffer on each DIMM to allow the DIMM bus to retrieve data although the data bus is currently busy. Additional functionality and use of the buffers are described in greater details below.

The high speed upstream memory bus 302 and downstream memory bus 304 exit from the lower portion of the buffer device 402, and connect to a memory controller or other memory modules either upstream or downstream of this memory module 306, depending on the application. The buffer device 402 (or more specifically, buffer logic 424) receives signals that are four times the memory module data rate and converts them into signals at the memory module data rate.

Figure 5:
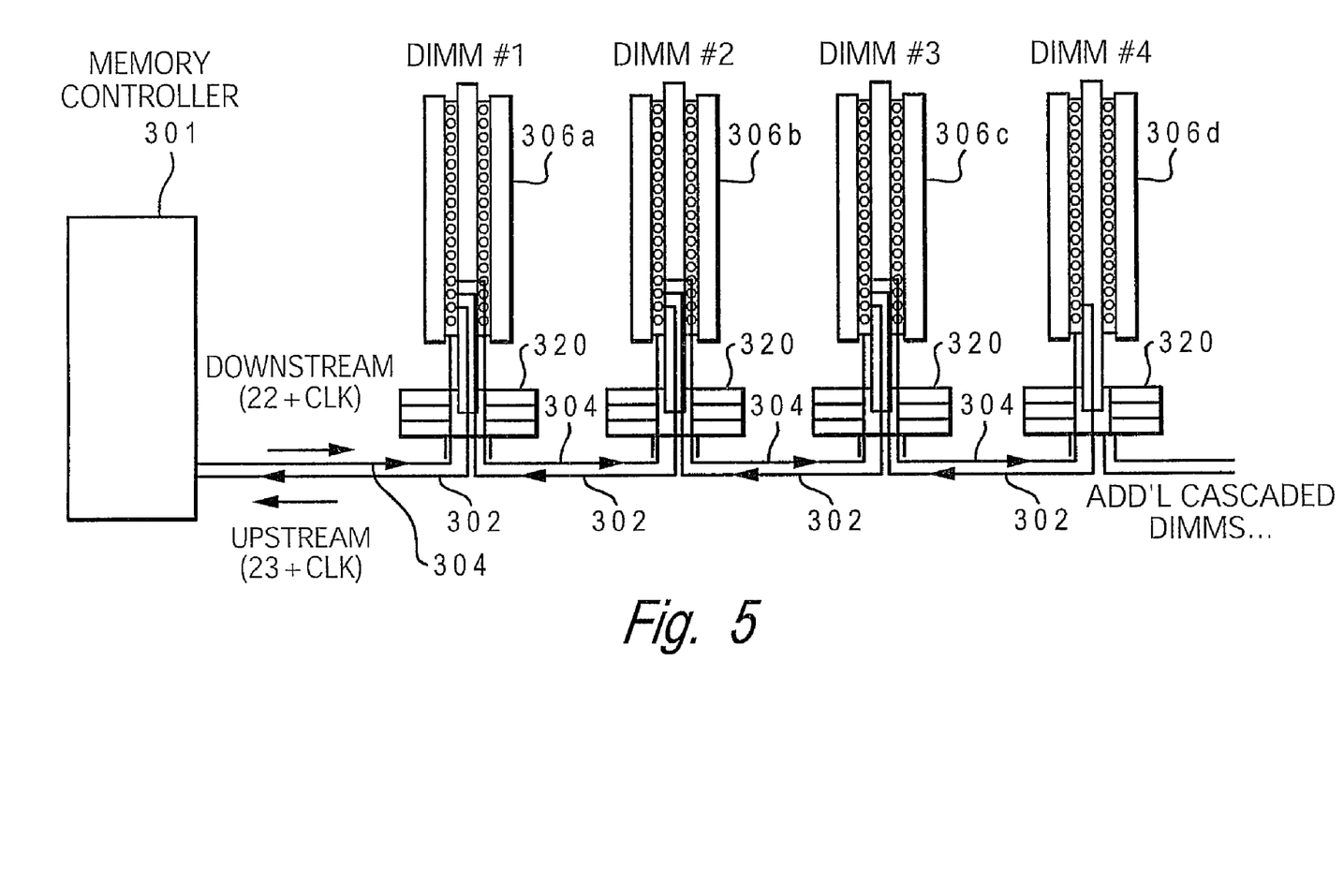
FIG. 5 illustrates cascaded memory modules of a memory subsystem with off-module read buffers within the backplane structure according to one embodiment of the invention.

FIG. 5 illustrates an alternate embodiment by which the functionality associated with buffers on the memory module maybe implemented. FIG. 5 provides a similar layout to FIG. 3A and like figures are numbered alike. Unlike FIG. 3A, which has a sequence of cascaded DIMMS with buffers on-module, the buffers 320, 322 and buffer logic (not shown) of FIG. 5 are provided on the backplane of the memory subsystem (i.e., off-module). This configuration enables memory modules to be dedicated to hosting memory devices and also enables larger buffer structures to support multiple buffered read data.

A full description of the process flow for providing positional read data latency is provided by the co-pending patent application (Ser. No. 10/903,178), which has been previously incorporated herein. Relevant portions of that description includes the description of the use of an outstanding read latency counter (ORLC) used by logic of the memory controller 301 to keep track of the remaining latency of the latest outstanding read operation, including all transfers of data within a burst. Also relevant is the description and use of a read data buffer delay (RDBD), which is an additional delay period, also referred to herein as an additional read data latency time period) for the target memory module that is calculated.

Each read command that is issued by the memory controller will have an associated RDBD value, which may be zero. This value is chosen to return all data to the memory controller 301 in a predetermined order defined by the memory controller and to prevent collisions on the read data return busses (i.e., the upstream memory bus 302). The smallest (optimal) allowed value is easily determined by subtracting the read latency configuration for the addressed, or target, memory module 306 from the current ORLC and adding one. Using the RDBD values from this formula, along with multiple read commands, results in the back-to-back return of read data with no collisions. Read commands issued to an idle memory channel, will always add zero RDBD so that data will be returned as quickly as possible.

Streaming Reads for Early Completion

While the above method eliminates the inefficiencies inherent with biasing all read operations to complete at a worst case latency within the memory modules, while still preventing data collisions on the memory channel, the present invention focuses on maximizing the utilization of both the memory channel and the data buses of the memory modules, as described below. Further, the invention provides even greater overall efficiency by hiding the busy states of the memory modules due to early completion of reads at the memory modules. Also, the invention allows parallel processing of reads across memory modules and thus eliminates delays in waiting for a memory bus to become idle before issuing a next read.

Busy states of a DRAM occur whenever the DRAM processes an operation (read/write) that requires data to be moved in or out of the DRAM. Once the data is moved, a given number of cycles is required for the DRAM lines to recharge and become ready to accept a next operation (i.e., go to an idle state). Since a next operation cannot be completed at the DRAM until the DRAM goes to the idle state, speeding up the time at which idle state is achieved is a desirable result, which is achieved by the invention. The period before the DRAM is able to accept a new operation is referred to as a busy period.

As described throughout, exemplary embodiments of the present invention allows read commands to be issued by the memory controller as soon as possible without having to allow gaps in the command stream to prevent read data collisions. These gaps that are inserted (or allowed) in the prior art processing of reads from the memory controller were inserted to prevent data bus collisions. In the present invention, read commands are issued on each read cycle as long as a read operation within the memory module targets a non-busy memory module. This enables multiple reads to be in flight within the memory subsystem at the same time, and enables the memory devices to return from a busy state early. The early completion of reads further enables the accessed memory cells to be recharged for another read operation early enough to substantially reduce the delays in getting data from the DRAM in order to fill up the system data bus. Thus, exemplary embodiments of the present invention significantly reduce the occurrence of holes in the system data bus (or upstream read data transmissions).

Figure 6:
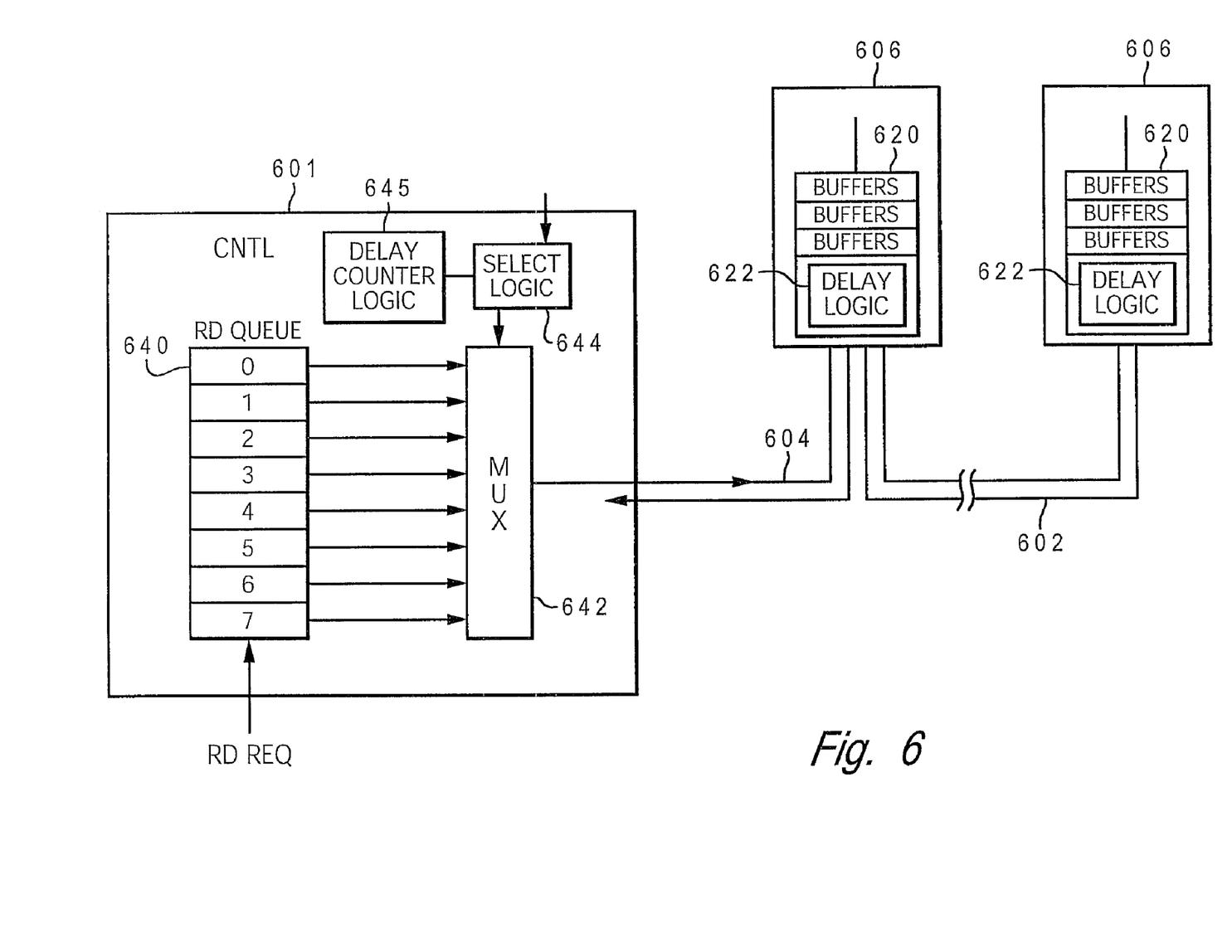
FIG. 6 depicts the memory controller with read reorder queue, select logic and delay counter logic in accordance with an exemplary embodiment of the present invention.

In order to accommodate the sequential issuing of multiple read commands being received at the memory controller targeting different memory modules, enhancements to the logic of memory controller are provided in the illustrative embodiment. FIG. 6 illustrates one possible configuration of the memory controller 601 and buffered memory modules 606 within a cascaded memory subsystem. As shown by FIG. 6, memory controller 601 includes a read queue 640, with eight slots for reads received at the memory controller 601. Memory controller 601 also includes a select logic 644 and a delay counter logic 645. Select logic 644 performs several functions, including: (1) track which memory modules are currently busy; (2) select the next read to be issued to the address/command/control bus; and (3) issue the next read at the next command cycle. In the illustrative embodiment, select logic 644 receives input from an external source that affects the selection process (either the read selected or the frequency of issuing new reads, e.g., every command cycle or every 2 command cycles, etc.).

Delay counter logic 645 provides the following functions: (1) track the number of delay cycles for a last issued read; (2) calculate a new number of delay cycles for a next scheduled read being issued to avoid any collisions on the memory channel; (3) associate the calculated delay value with the next scheduled read, such that the delay value is sent to the logic of the corresponding memory module; and (4) track the time to idle (TTI) for each memory module (i.e., the number of cycles before a busy memory module becomes idle).

The value of TTI enables a read targeting a particular memory module to be issued on a next read cycle that corresponds to X cycles before the memory module returns from the busy state following a previous read (or write) operation. In the illustrative embodiment, the value of X is the number of cycles required for the issued read command to reach the memory module. Thus, the read is issued while the memory module is still busy but arrives at the memory module just as the memory module goes to an idle state.

Unlike the RDBD of the related applications, which provides a delay directly correlated to the latency for returning the data of the previously issued read, the delay parameter of the present invention includes additional cycles because of the early processing of the read operations at the memory module. With multiple buffers at each memory module, it is conceivable that the read data has a delay value equal to the sum of multiple RDBDs if the read data is placed in one of the last available read buffers.

Returning now to FIG. 6, memory controller includes a MUX 642 utilized to enable select logic 644 to select any one of the available reads within the read queue 640. Select logic 644 determines, based on an analysis of the current utilization of the individual DIMMs within the memory subsystem, which of the N possible reads to issue next to the address/command/control system bus 604. The current utilization indicates which, if any, of the memory modules 606 is currently busy and is thus unable to handle a next scheduled read operation. Notably, as mentioned above, a "busy" memory module is not necessarily eliminated from receiving a next read, particularly if the memory module will be able to return to an idle state before a next issued read operation arrives at the memory module.

The read commands are issued to the memory subsystem in any order. Once select logic 644 completes its analysis and identifies one or more reads that are eligible to be issued to idle (or soon to be idle) memory modules with available buffers, the selection logic will issue the read to the memory channel. Additional read commands that are identified as targeting memory banks or modules that are not busy will be issued in a sequential manner without gaps in the command cycles. In one embodiment, priority is given to the oldest command within the queue, and thus a measure of the time order for each read is also maintained by the selection logic.

Figure 7A:
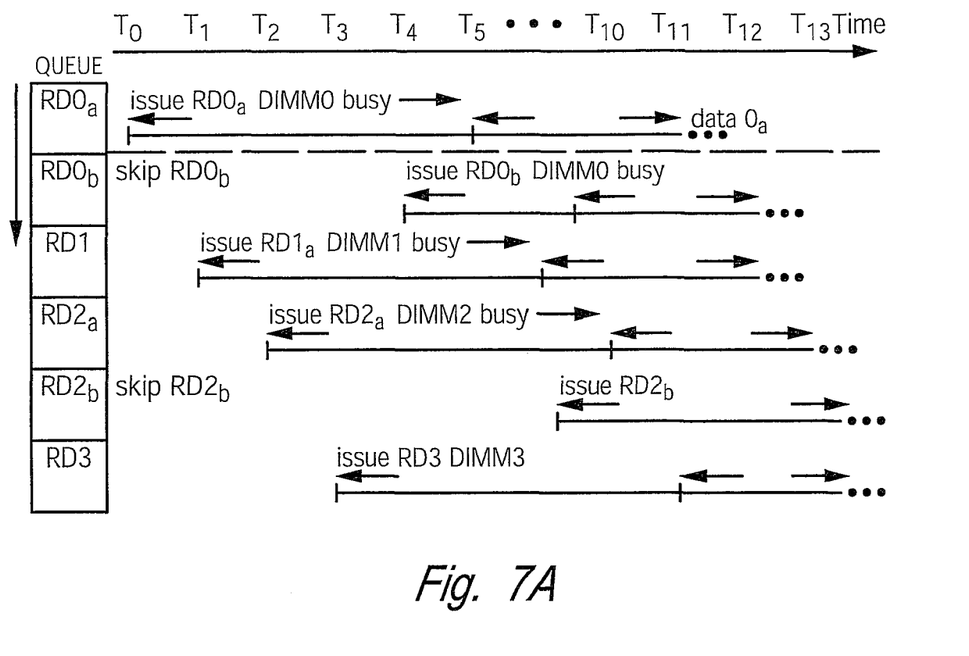
FIG. 7A is a timing diagram illustrating the issuing of reads to idle memory modules on sequential command cycles, according to one illustrative embodiment of the invention.
Figure 7B:
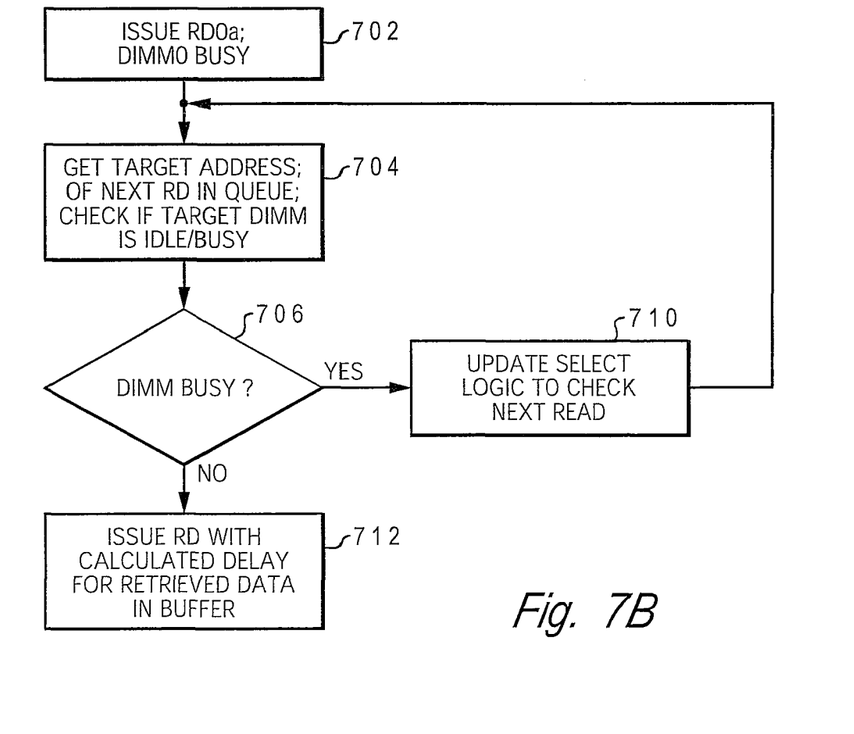
FIG. 7B is a flow chart of the process of issuing reads in sequence to enable parallel, early processing of reads within the memory subsystem according to one embodiment of the present invention.

Referring now to FIGS. 7A and 7B, FIG. 7A illustrates a time line for several reads (RD0$a$, RD0$b$, RD1, RD2$a$, RD2$b$, RD0$c$ and RD3) that are received sequentially at the memory controller. The numbers indicate the corresponding DIMM to which the reads are addressed, i.e., DIMM0, DIMM1, DIMM2, and DIMM3. Subscripted letters indicate several reads targeting the same memory module. These reads are received according to their alphabetical order. For example, RD0$a$ and RD0$b$ represent two read targeting the same memory module, DIMM0, with RD0$a$ being received first. For illustration, time T0, T1, etc, are assumed to be command cycles and not actual clock cycles. Thus if each read command takes 4 clock cycles to be issued to the address/command bus, T1 is exactly 4 clock cycles after T0, T2 is also 4 clock cycles after T1, and so on.

Similar to those described above, each memory module has multiple read buffers utilized to delay the retrieved data a pre-calculated number of cycles. As also described above, selection logic within the memory controller selects a next earliest received read that targets an idle (or soon to be idle) memory module and associates a delay parameter with that read command.

FIG. 7B provides a flow chart of the process of selecting the reads and issuing the reads early based on the business of the corresponding memory modules. As is illustrated by the figures, when an earlier received read targets a busy memory module, the next reads targeting idle memory modules are selected out of order and issuing to the system bus. This enables greater utilization of idle bus bandwidth (at the memory modules) and thus maximizes the overall bus utilization of the memory channel. Also, the presence of a busy memory module does not hold up the early processing of latter reads at other memory modules.

Turning now to the figures, at time T0 (corresponding to block 702), RD0a is first issued to DIMM0 and causes the target memory module (DIMM0) to go into a busy state as RD0a is processed. DIMM0 receives RD0 and initiates a process to the retrieve the requested for data and buffer/return the data. DIMM0 remains busy until the DRAM recharges (time T4), although the data is only returned some time later (T18), where that time is based on the delay parameter associated with the read command. Once RD0a is issued, the select logic obtains the target address of the next read in the queue (block 704) and then determines whether the corresponding memory module is in an idle (or soon to be idle) state (block 706). If the target memory module is busy, the logic moves on to the next read in the read queue (block 710). The select logic iterates through this checking process until it locates a read request within the read queue targeting an idle memory module.

In one embodiment, the select logic tracks the busy state of each memory module. When selecting a next read, the logic compares the target address of the read to the list of busy/idle DIMMs. According to the illustration, RD0b is the next request in line (based on the time received by the memory controller). However, the selection logic recognizes that the target memory module, DIMM0, is busy. RD1 in, contrast, targets data in DIMM1, which is currently idle.

At time T1, the select logic issues the next read (i.e., RD1) within the queue with an idle target memory module (DIMM1) (block 712). The issued read includes the calculated delay for retrieved data that is to be stored within a buffer. The delay value is 0 and the data is not buffered for earlier reads or when the memory channel is not being utilized and has no read data scheduled to be placed thereon.

Notably, RD0b is skipped since DIMM0 is busy at time T1. RD2a is then issued at the next command cycle T2, RD2b is skipped and RD3 issued at time T3. At time T4, DIMM0 enters the soon to be idle state and DIMM0 becomes idle at time T5. Thus, RD0b is issued at time T4 or T5 depending on the specific implementation being utilized.

According to the timing diagram, at times T3 and T4, all four DIMMs are processing reads in a somewhat parallel mode. The overlap occurs because the time to process the reads at the memory modules is longer than the transmission latency of each read command. DIMM0 moves to an idle state at time T5, DIMM1 at time T6, etc., so the cycle of issuing reads in sequence may be completed again. The cycle at which data is returned is, however, DIMM-specific, and is thus different for each memory module.

In the prior art, the memory controller waits until DIMM0 is no longer busy before issuing RD0b, and RD1 is only issued after RD0a had been processed. With the present invention, however, the selection logic picks RD1 as the next read to issue, and RD1 is issued to the memory modules at the next command cycle. RD0b is retained within the read reorder buffer until DIMM0 is no longer busy. Then, RD0b is issued to DIMM0.

The next read command targeting the DIMM may be sent to the DIMM while the data of the previous read command is still within the DIMM's buffer. Each data stored in respective buffers have their corresponding delay times. If all the buffers of a memory module are filled, the memory module is made to appear busy by the selection logic so that no further reads are sent to that memory module until the data of at least one of the buffers is placed on the memory channel.

As shown by the timing diagram, RD1 triggers DRAM1 to initiate data retrieval almost immediately after RD0 initiates its data retrieval. However, the data that is retrieved from each DRAM is immediately placed within the respective read data buffers and not placed on the data bus until the delay period expires. Since the delay period is pre-calculated to prevent any collisions on the memory channel, the data of RD1 is not placed on the memory channel until after the predetermined number of cycles required for the data of RD0 to be placed on the memory channel.

Improved efficiency in utilization of both the memory channel and memory module buses are provided by the above described streaming of consecutive reads to idle memory modules. Retries on the address/command/control bus are substantially eliminated, while bandwidth on the data bus of an idle memory module is more quickly allocated for use and reuse. Additionally, the usage of the read buffers at the memory module enables actual time delays that enable the early retrieved data does not cause a collision on the memory channel.

One feature of the invention enables parallel processing of reads that are streamed to multiple buffered memory modules on consecutive read cycles. Multiple DIMMs actively process read operations early and then become idle early to enable even earlier processing of later reads. One benefit of this approach is that the depth of the read queue may be decreased as the reads are streamed to the memory modules almost as soon as they arrive at the memory controller.

With the address/command/control bus being utilized for every command cycle (while there are reads within the read queue targeting idle DIMMs) and both the memory channel and memory module data buses being continuously fed with retrieved data, very few holes occur on the memory channel, and the invention allows the overall utilization of the memory channel and memory module's buses to be maximized, while effectively hiding busy periods on the memory modules.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A cascaded memory subsystem comprising:
one or more memory modules each having a read buffer, control logic, one or more memory devices, and a data bus for retrieving data from the one or more memory devices;
a memory controller including logic for selecting a next read command that is not targeting a busy memory module and immediately forwarding the next read command to the memory module at the next command cycle;
a memory channel connecting the memory controller to the one or more memory modules via point-to-point buses; and
means for issuing read commands to the memory channel on command cycles, wherein each issued read command targets a memory module that is not busy, and said read commands initiate a retrieval of read data on one or more of said memory modules in parallel.

2. The memory subsystem of claim 1, wherein said command cycles are substantially sequential and includes each command cycle at which there is an idle memory module, wherein read commands are issued early relative to the time the retrieved data may be placed on the memory channel, and wherein each of said command cycles is selected so as to maximize use of the data bus internal to the one or more memory modules and make the memory modules return to an idle state and be available for handling subsequent reads earlier.

3. The memory subsystem of claim 1, further comprising:
means for including a delay period within the read command, said delay period being a number of cycles that data retrieved from the one or more memory devices is held at the memory module before being placed on the memory channel; and
means for buffering the data retrieved in one of the read buffers of the memory module; and
means for issuing the data to the memory channel when the delay period expires.

4. The memory subsystem of claim 3, wherein the delay period is calculated at the memory controller to enable the data to be placed at a first available hole on the memory channel following a return of all read data retrieved by all previously issued read commands.

5. The memory subsystem of claim 1, wherein said memory controller comprises:
select logic for selecting a next read command to issue to the memory channel, wherein said select logic selects a next available read that is not targeting a busy memory module and delays issuing read commands targeting a busy memory module, such that the read commands may be issued out-of-order relative to the time the read commands are received at the memory controller; and
logic for calculating the delay period to assign to a next read command to be issued, said logic providing a delay period that maximizes the use of the memory channel bandwidth to initiate a return of the data as soon as the memory channel receives a last data from the previously issued read command.

6. The memory subsystem of claim 1, said control logic of said one or more memory modules comprising:
logic for storing the data retrieved by a read command in one of the read buffers until the delay period expires, wherein the data is immediately placed on the memory channel when the delay period expires prior to the data being retrieved and the data is placed in the read buffer only when the delay period has not yet expired; and
logic for tracking the delay period and issuing the data to the memory channel when the delay period expires.

7. The memory subsystem of claim 1, said memory channel having a unique transmission latency for each memory module, with a first transmission latency for a first module and a second longer transmission latency for a second module, said memory controller further comprising:
means for determining when data of a next issued read command may be retrieved and placed on the memory channel before data of a previously issued read command is ready to be placed on the memory channel; and
when the memory channel is free, providing a zero delay period for the next issued read command so that the data retrieved by the next issued read command is returned ahead of the data of the previously issued read command; and
associating a first returned data to the next issued read command and a second returned data to the previously issued read command, such that data is returned out-of-order relative to the issuance of corresponding read commands to the memory channel.

8. The memory subsystem of claim 1, wherein said buffers are located on a back plane to which the one or more memory modules are electrically coupled.

9. A data processing system comprising:
a processor that issues read commands; and
a memory subsystem coupled to said processor and which receives and processes said read commands, said memory subsystem having:
a memory controller;
multiple memory modules each having one or more memory devices, control logic, and a data bus for transmitting data to and from the memory devices;
a memory channel connecting the multiple memory modules to each other and to the memory controller, said channel having a daisy chain, point-to-point bus configuration;
a plurality of read buffers associated with each memory module and utilized to temporarily store retrieved read data before placing the read data on the memory channel; and
wherein said memory controller forwards read commands targeting idle memory modules at substantially each command cycle such that issued read commands complete a retrieval of read data at the memory devices early and said memory modules are made ready to process a next read operation before the read data is required to be placed on the memory channel.

10. The data processing system of claim 9, wherein the read buffers are located on the memory modules.

11. The data processing system of claim 9, wherein the read buffers are located on a backplane to which the memory modules are electrically coupled.

12. The data processing system of claim 9, wherein said command cycles are substantially sequential and includes each command cycle at which there is an idle memory module, wherein read commands are issued early relative to the time the retrieved data may be placed on the memory channel, and wherein each of said substantially sequential command cycles is selected so as to maximize use of the data bus internal to the one or more memory modules and make the memory modules return to an idle state and be available for handling subsequent reads earlier.

13. The data processing system of claim 9, said memory subsystem further comprising:
means for including a delay period within the read command, said delay period being a number of cycles that data retrieved from the one or more memory devices is held at the memory module before being placed on the memory channel;

means for buffering the data retrieved in one of the read buffers of the memory module; and means for issuing the data to the memory channel when the delay period expires.

14. The data processing system of claim 13, wherein the delay period is calculated at the memory controller to enable the data to be placed at a first available hole on the memory channel following a return of all read data retrieved by all previously issued read commands.

15. The data processing system of claim 9, wherein said memory controller comprises:

select logic for selecting a next read command to issue to the memory channel, wherein said select logic selects a next available read that is not targeting a busy memory module and delays issuing read commands targeting a busy memory module, such that the read commands may be issued out-of-order relative to the time the read commands are received at the memory controller; and logic for calculating the delay period to assign to a next read command to be issued, said logic providing a delay period that maximizes the use of the memory channel bandwidth to initiate a return of the data as soon as the memory channel receives a last data from the previously issued read command.

16. The data processing system of claim 9, said control logic of said one or more memory modules comprising:

logic for storing the data retrieved by a read command in one of the read buffers until the delay period expires, wherein the data is immediately placed on the memory channel when the delay period expires prior to the data being retrieved and the data is placed in the read buffer only when the delay period has not yet expired; and logic for tracking the delay period and issuing the data to the memory channel when the delay period expires.

17. The data processing system of claim 9, said memory channel having a unique transmission latency for each memory module, with a first transmission latency for a first module and a second longer transmission latency for a second module, said memory controller further comprising:

means for determining when data of a next issued read command may be retrieved and placed on the memory channel before data of a previously issued read command is ready to be placed on the memory channel;

when the memory channel is free, providing a zero delay period for the next issued read command so that the data retrieved by the next issued read command is returned ahead of the data of the previously issued read command; and associating a first returned data to the next issued read command and a second returned data to the previously issued read command, such that data is returned out-of-order relative to the issuance of corresponding read commands to the memory channel.

* * * * *